United States Patent
Bourgeois et al.

(10) Patent No.: US 7,485,741 B2
(45) Date of Patent: Feb. 3, 2009

(54) METHOD OF PRODUCING NITRILE COMPOUNDS FROM ETHYLENICALLY-UNSATURATED COMPOUNDS

(75) Inventors: Damien Bourgeois, Lyons (FR); Jean-Christophe Galland, Lyons (FR); Blaise Didillon, Francheville (FR); Philippe Marion, Vernaison (FR)

(73) Assignee: Rhodia Polyamide Intermediates, Saint-Fons (FR)

( * ) Notice: Subject to any disclaimer, the term of this patent is extended or adjusted under 35 U.S.C. 154(b) by 324 days.

(21) Appl. No.: 10/537,260

(22) PCT Filed: Nov. 25, 2003

(86) PCT No.: PCT/FR03/03475

§ 371 (c)(1), (2), (4) Date: Oct. 14, 2005

(87) PCT Pub. No.: WO2004/060855

PCT Pub. Date: Jul. 22, 2004

(65) Prior Publication Data

US 2006/0142609 A1    Jun. 29, 2006

(30) Foreign Application Priority Data

Dec. 2, 2002   (FR)  .................. 02 15115

(51) Int. Cl.
*C07C 253/00* (2006.01)

(52) U.S. Cl. ............. 558/335; 558/332; 502/162

(58) Field of Classification Search ............ 558/335, 558/332; 502/162
See application file for complete search history.

(56) References Cited

U.S. PATENT DOCUMENTS 7,084,293 B2 *   8/2006   Rosier et al. ............ 558/335

FOREIGN PATENT DOCUMENTS

| DE | 101 40 083 | 2/2003 |
|---|---|---|
| EP | 1 201 675 | 5/2002 |
| FR | 2 338 253 | 8/1977 |
| WO | WO/2001/21580 | 3/2001 |
| WO | WO/1995/30680 | 11/2005 |

OTHER PUBLICATIONS

Soliman et al., 1997, CAS: 126:293386.*
Selent, D. et al., "New Phosphorus Ligands for the Rhodim-Catalyzed Isomerization/Hydroformylation of Internal Octenes", *Angewandte Chemie*, vol. 40, No. 9, May 4, 2001.

* cited by examiner

*Primary Examiner*—Rei-tsang Shiao
(74) *Attorney, Agent, or Firm*—Buchanan, Ingersoll & Rooney, P.C.

(57) ABSTRACT

The present invention relates to a process for hydrocyanating a hydrocarbon-based compound containing at least one ethylenic unsaturation by reaction in liquid medium with hydrogen cyanide in the presence of a catalyst comprising a metal element chosen from transition metals and an organophosphorus ligand, characterized in that the organophosphorus ligand is a monodentate organophosphorus compound. The present invention is in particular useful for the synthesis of adiponitrile from butadiene.

19 Claims, No Drawings

METHOD OF PRODUCING NITRILE COMPOUNDS FROM ETHYLENICALLY-UNSATURATED COMPOUNDS

This application is an application under 35 U.S.C. Section 371 of International Application Number PCT/FR2003/003475 filed on Nov. 25, 2003.

The present invention relates to a process for hydrocyanating an ethylenically unsaturated organic compounds to compounds containing at least one nitrile function.

It relates more particularly to the hydrocyanation of diolefins such as butadiene or of substituted olefins such as alkenenitriles, for instance pentenenitriles.

French Patent No. 1 599 761 describes a process for preparing nitrites by addition of hydrocyanic acid with organic compounds having at least one ethylenic double bond, in the presence of a nickel catalyst and of a triaryl phosphite. This reaction can be carried out in the presence or absence of a solvent.

When a solvent is used in this process of the prior art, it is preferably a hydrocarbon, such as benzene or xylenes, or a nitrile such as acetonitrile.

The catalyst used is an organic complex of nickel, containing ligands such as phosphines, arsines, stibines, phosphites, arsenites or antimonites.

The presence of a promoter for activating the catalysts, such as a boron compond or metal salt, generally a Lewis acid, is also recommended in said patent.

Patent FR-A-2 338 253 has proposed carrying out the hydrocyanation of compounds having at least one ethylenic unsaturation in the presence of an aqueous solution of a compound of a transition metal, in particular nickel, palladium or iron, and of a sulphonated phosphine.

The sulphonated phosphines described in that patent are sulphonated triarylphosphines, and more particularly sulphonated triphenylphosphines.

This process allows correct hydrocyanation, in particular of butadiene and of pentenenitriles, and easy separation of the catalytic solution, by simple settling out, and consequently avoids as much as possible the discharge of effluents or of waste containing the metals used as catalyst.

Research has, however, been carried out in order to find new catalytic systems which give greater performance in terms of catalytic activity and of stability.

One of the aims of the present invention is to propose a new family of ligands which, with the transition metals, make it possible to obtain catalytic systems exhibiting improved activity compared with the known systems.

To this effect, the present invention proposes a process for hydrocyanating a hydrocarbon-based compound containing at least one ethylenic unsaturation by reaction in a liquid medium with hydrogen cyanide in the presence of a catalyst comprising a metallic element chosen from transition metals and an organophosphorus ligand, characterized in that the organophosphorus ligand corresponds to general formula (I) below:

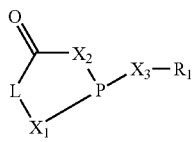

in which:

$X_1$ and $X_2$, which may be identical or different, represent an oxygen atom or the divalent radical NR2, in which R2 represents a hydrogen atom or an alkyl, aryl, sulphonyl, cycloalkyl or carbonyl radical, $X_3$ represents a covalent bond, an oxygen atom or the divalent radical NR2, in which R2 represents a hydrogen atom or an alkyl, aryl, sulphonyl, cycloalkyl or carbonyl radical, the radical $R_1$ represents a linear or branched alkyl radical having from 1 to 12 carbon atoms that may contain hetero atoms, or a substituted or unsubstituted aromatic or cycloaliphatic radical that may contain hetero atoms or one or more rings in fused or nonfused form, L represents a linear or branched divalent alkyl radical having from 1 to 12 carbon atoms that may contain hetero atoms, or a substituted or unsubstituted aromatic or cycloaliphatic divalent radical that may contain hetero atoms and one or more rings in fused or nonfused form.

In a preferred embodiment, $X_1$ and $X_2$ are different and represent equally an oxygen atom or a divalent radical NR2.

Preferably, the bonds of the divalent radical are in the ortho-position in the case of an aromatic radical or carried by the same carbon or two carbons in the alpha-position with respect to one another in the case of an acyclic or cyclic alkyl radical.

Moreover, in a preferred embodiment of the invention $X_3$ represents oxygen.

In addition, L advantageously represents:

- a derivative of salicylamide, optionally functionalized on the aromatic ring, and/or by formation of the aliphatic or aromatic secondary amide, for instance salicylanilide or naphtol AS.
- a derivative of anthranilic acid, substituted on the aromatic ring, and/or by formation of the aliphatic or aromatic secondary amine, for instance N-phenylanthranilic acid or N-methyl anthranilic acid,
- an alpha amino acid, more preferably a natural amino acid derivative in which the nitrogen atom is monosubstituted with an aliphatic, aromatic, aryl sulphonyl or carbonyl group.

These compounds can be obtained by reacting, in the presence of a base, a compound A of formula (II) below:

with an appropriate halophosphorus, more particularly chlorophosphorus, derivative of formula (III) below:

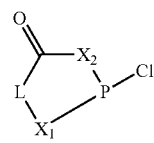

The halophosphorus derivative can be obtained by reacting PCl₃ with a compound of formula (IV) below:

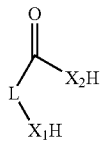

Such structures of formula (IV) that are preferred can correspond to the compounds below:

salicylamide

salicylanilide

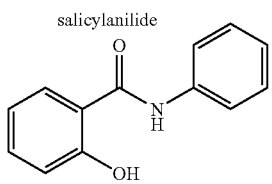

Naphtol AS

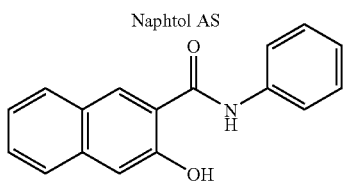

N-phenylanthranilic acid

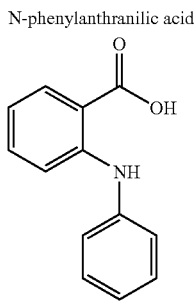

anthranilic acid

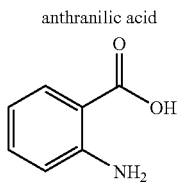

The compounds of formula (I) can be obtained by means of other processes, in particular when $X_3$ represents a covalent bond.

By way of examples of compounds of general formula I, mention may be made of the compounds listed below (in the following formulae, the symbol Me signifies the methyl radical, and the symbol tBu signifies the tert-butyl radical):

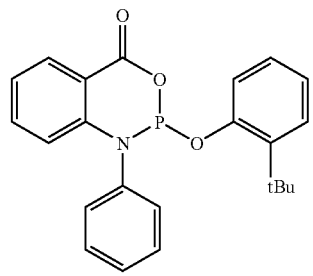

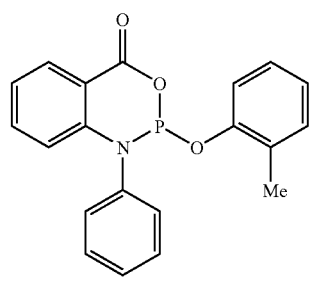

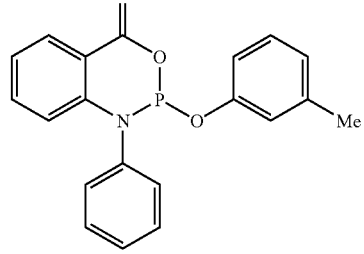

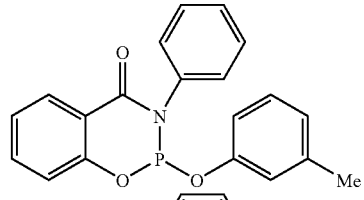

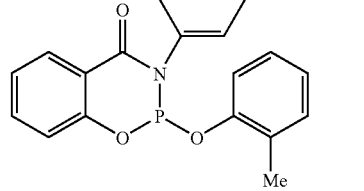

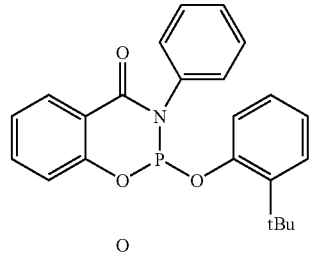

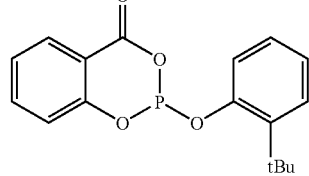

According to a preferred characteristic of the invention, the metal element is chosen from the group comprising nickel, cobalt, iron, ruthenium, rhodium, palladium, osmium, iridium, platinum, copper, silver, gold, zinc, cadmium and mercury. Among these metals, nickel is the preferred metal.

According to the invention, the catalyst advantageously corresponds to general formula (V):

$$M[L_f]_t \qquad (V)$$

in which:

M is a transition metal, $L_f$ represents the organophosphorus ligand of formula (I) and t represents a number between 1 and 6 (limits inclusive).

The organometallic complexes containing the compounds of formula (I) can be prepared by bringing a solution of a compound of the metal selected into contact with a solution of a compound of formula (I).

The compound of the metal can be dissolved in a solvent.

In the compound used, the metal may be in the oxidation state that it will have in the organometallic complex, or in a higher oxidation state.

By way of example, it may be indicated that, in the organometallic complexes of the invention, rhodium is in oxidation state (I), ruthenium in oxidation state (II), platinum in oxidation state (0), palladium in oxidation state (0), osmium in oxidation state (II), iridium in oxidation state (I), and nickel in oxidation state (0).

If, during the preparation of the organometallic complex, the metal is used in a higher oxidation state, it may be reduced in situ.

The organometallic complexes comprising the compounds of formula (I) can be used as catalysts in olefin hydrocyanation reactions or the hydrocyanation of unsaturated compounds containing, for example, a nitrile function.

As transition metal, use is preferably made of the compounds of transition metals, more particularly the compounds of nickel, of palladium, of iron or of copper.

Among the abovementioned compounds, the most preferred compounds are those of nickel.

By way of non-limiting examples, mention may be made of:

compounds in which nickel is in oxidation state zero, such as potassium tetracyanonickelate $K_4[Ni(CN)_4]$, bis (acrylonitrile)nickel zero, bis(cycloocta-1,5-diene) nickel (also called $Ni(cod)_2$) and derivatives containing ligands, such as tetrakis(triphenylphosphine)nickel zero;

compounds of nickel such as carboxylates (in particular acetate), carbonate, bicarbonate, borate, bromide, chloride, citrate, thiocyanate, cyanide, formate, hydroxide, hydrophosphite, phosphite, phosphate and derivatives, iodide, nitrate, sulphate, sulphite, aryl- and alkylsulphonates.

When the nickel compound used corresponds to a nickel oxidation state greater than zero, a nickel-reducing agent that reacts preferentially with the nickel under the reaction conditions is added to the reaction medium. This reducing agent may be organic or inorganic. As non-limiting examples, mention may be made of borohydrides such as $BH_4Na$ or $BH_4K$, Zn powder, magnesium or hydrogen.

When the nickel compound used corresponds to the zero oxidation state of nickel, it is also possible to add a reducing agent of the abovementioned type, but such addition is not mandatory.

When an iron compound is used, the same reducing agents are suitable.

In the case of palladium the reducing agents may, in addition, be elements of the reaction medium (phosphine, solvent, olefin).

The organic compounds containing at least one ethylenic double bond that are more particularly used in the present process are diolefins such as butadiene, isoprene, hexa-1,5-diene, cycloocta-1,5-diene, ethylenically unsaturated aliphatic nitriles, particularly linear pentenenitriles such as 3-pentene-nitrile or 4-pentenenitrile, monoolefins such as styrene, methylstyrene, vinylnaphthalene, cyclohexene, methylcyclohexene, and mixtures of several of these compounds.

The pentenenitriles in particular may contain amounts, generally minor amounts, of other compounds, such as 2-methyl-3-butenenitrile, 2-methyl-2-butenenitrile, 2-pentenenitrile, valeronitrile, adiponitrile, 2-methylglutaronitrile, 2-ethylsuccinonitrile or butadiene, originating, for example, from the prior hydrocyanation reaction of the butadiene to unsaturated nitriles.

The reason for this is that the hydrocyanation of butadiene is accompanied by the formation, along with the linear pentenenitriles, of not insignificant amounts of 2-methyl-3-butenenitrile and 2-methyl-2-butenenitrile.

The catalyst system used for the hydrocyanation according to the process of the invention may be prepared before it is introduced into the reaction zone, for example by adding the appropriate amount of selected transition metal compound and, optionally, of reducing agent to the compound of formula (I), alone or dissolved in a solvent. It is also possible to prepare the catalyst system "in situ" by simply adding the compound of formula (I) and the transition metal compound to the hydrocyanation reaction medium before or after adding the compound to be hydrocyanated.

The amount of compound of nickel or of another transition metal used is chosen so as to give a concentration, in moles of transition metal per mole of organic compounds to be hydrocyanated or isomerized, of between $10^{-4}$ and 1, preferably of between 0.005 and 0.5 mol of nickel or of the other transition metal used.

The amount of compound of formula (I) used to form the catalyst is chosen such that the number of moles of this compound, relative to 1 mol of transition metal, is from 0.5 to 500, and preferably from 2 to 100.

Although the reaction is generally carried out without solvent, it may be advantageous to add an inert organic solvent. The solvent may be a solvent for the catalyst which is miscible with the phase comprising the compound to be hydrocyanated, at the hydrocyanation temperature. By way of examples of such solvents, mention may be made of aromatic, aliphatic or cycloaliphatic hydrocarbons.

The hydrocyanation reaction is generally carried out at a temperature of 10° C. to 200° C., and preferably of 30° C. to 120° C. It may be carried out in a single-phase or in a two-phase medium.

The process of the invention may be carried out continuously or batchwise.

The hydrogen cyanide used may be prepared from metal cyanides, in particular sodium cyanide, or from cyanohydrins, such as acetone cyanohydrin, or by any other known synthesis process.

The hydrogen cyanide is introduced into the reactor in gaseous form or in liquid form. It may also be dissolved beforehand in an organic solvent.

In the context of a batchwise implementation, it is possible in practice to charge a reactor, purged beforehand by means of an inert gas (such as nitrogen or argon), either with a solution containing all or a part of the various constituents, such as the compound to be hydrocyanated, the compounds of formula (I), the transition metal compound, the optional reducing agent and solvent, or with said constituents separately. Generally, the reactor is then taken to the selected temperature. The hydrogen cyanide is then itself introduced, preferably continuously and regularly.

When the reaction (whose development can be monitored by assaying samples) is at an end, the reaction mixture is withdrawn, after cooling, and the reaction products are isolated, by distillation for example.

An enhancement of the process for hydrocyanating ethylenically unsaturated compounds according to the present invention relates in particular to the hydrocyanation of said ethylenically unsaturated nitrile compounds by reaction with hydrogen cyanide and consists in using a catalyst system in accordance with the present invention with a cocatalyst consisting of at least one Lewis acid.

The ethylenically unsaturated compounds that may be used in this enhancement are in general those that were mentioned for the basic process. However, it is more particularly advantageous to apply it to the reaction consisting of hydrocyanation of ethylenically unsaturated aliphatic nitrites to dinitriles, in particular apply it to the linear pentenenitriles such as 3-pentenenitrile or 4-pentenenitrile, and mixtures thereof.

These pentenenitriles may contain amounts, generally minor amounts, of other compounds, such as 2-methyl-3-butenenitrile, 2-methyl-2-butenenitrile, 2-pentene-nitrile, valeronitrile, adiponitrile, 2-methylglutaro-nitrile, 2-ethylsuccinonitrile or butadiene, originating from the prior hydrocyanation reaction of the butadiene and/or from the isomerization of 2-methyl-3-butenenitrile to pentenenitriles.

The Lewis acid used as cocatalyst makes it possible in particular, in the case of the hydrocyanation of ethylenically unsaturated aliphatic nitrites, to improve the linearity of the dinitriles obtained, i.e. the percentage of linear dinitriles relative to the total dinitriles formed, and/or to increase the activity and service life of the catalyst.

In the present text, the term "Lewis acid" is intended to mean, according to the usual definition, compounds that accept electron pairs.

Use may in particular be made of the Lewis acids mentioned in the work edited by G. A. Olah, "Friedel-Crafts and related Reactions", volume I, pages 191 to 197 (1963).

The Lewis acids that may be used as cocatalysts in the present process are chosen from compounds of the elements of groups Ib, IIb, IIIa, IIIb, IVa, IVb, Va, Vb, VIIb, VIIb and VIII of the Periodic Table of Elements. These compounds are most often salts, especially halides, such as chlorides or bromides, sulphates, sulphonates, haloalkylsulphonates, perhalo-alkylsulphonates, especially fluoroalkylsulphonates or perfluoroalkylsulphonates, haloalkylacetates, perhalo-alkylacetates, carboxylates and phosphates.

By way of non-limiting examples of such Lewis acids, mention may be made of zinc chloride, zinc bromide, zinc iodide, manganese chloride, manganese bromide, cadmium chloride, cadmium bromide, stannous chloride, stannous bromide, stannous sulphate, stannous tartrate, indium trifluoromethylsulphonate, indium trifluoro-methyl acetate, the chlorides or bromides of rare earth elements such as lanthanum, cerium, praseodymium, neodymium, samarium, europium, gadolinium, terbium, dysprosium, hafnium, erbium, thallium, ytterbium and lutetium, and cobalt chloride, ferrous chloride and yttrium chloride.

As a Lewis acid it is also possible to use organometallic compounds such as triphenylborane or titanium isopropoxide.

Mixtures of several Lewis acids can of course be used.

Among Lewis acids, zinc chloride, zinc bromide, stannous chloride, stannous bromide, triphenylborane, and zinc chloride/stannous chloride mixtures are most particularly preferred.

The Lewis acid cocatalyst used generally represents from 0.01 to 50 mol per mole of transition metal compound, more particularly of nickel compound, and preferably from 1 to 10 mol per mole.

As for the implementation of the basic process of the invention, the catalyst solution used for the hydrocyanation in the presence of Lewis acid may be prepared prior to its introduction into the reaction zone, or in situ, for example by adding the various components of the catalyst system to the reaction medium.

It is also possible, under the conditions of the hydrocyanation process of the present invention, and in particular by working in the presence of the above-described catalyst comprising at least one compound of formula (I) and at least one transition metal compound, to carry out the isomerization of 2-methyl-3-butene-nitrile to pentenenitriles, and more generally of branched unsaturated nitrites to linear unsaturated nitrites, in the absence of hydrogen cyanide.

The 2-methyl-3-butenenitrile subjected to the isomerization according to the invention may be used alone or as a mixture with other compounds.

Thus 2-methyl-3-butenenitrile may be deployed as a mixture with 2-methyl-2-butenenitrile, 4-pentene-nitrile, 3-pentenenitrile, 2-pentenenitrile, butadiene, adiponitrile, 2-methylglutaronitrile, 2-ethylsuccinonitrile or valeronitrile.

It is particularly advantageous to treat the reaction mixture originating from the hydrocyanation of butadiene with HCN in the presence of at least one compound of formula (I) and of at least one transition metal compound, more preferably of a compound of nickel in oxidation state 0, as defined above.

In the context of this preferred variant, since the catalyst is already present for the butadiene hydrocyanation reaction, it is sufficient to stop any introduction of hydrogen cyanide in order to allow the isomerization reaction to take place.

It is possible, where appropriate, in this variant to effect a gentle purging of the reactor by means of an inert gas, such as nitrogen or argon for example, in order to expel the hydrocyanic acid which might still be present.

The isomerization reaction is generally carried out at a temperature of 10° C. to 200° C., and preferably of 60° C. to 180° C.

In the preferred case of an isomerization immediately following the butadiene hydrocyanation reaction it will be advantageous to operate at the temperature at which the hydrocyanation was carried out.

As for the process for hydrocyanating ethylenically unsaturated compounds, the catalyst system used for the isomerization may be either already present in the medium or may be prepared according to the preparation methods already described above.

Although the isomerization reaction is generally carried out without solvent, it may be advantageous to add an inert organic solvent, which may be that of the subsequent extraction. This is in particular the case when such a solvent has been used in the butadiene hydrocyanation reaction that served to prepare the medium subjected to the isomerization reaction. Such solvents can be chosen from those that were mentioned above for the hydrocyanation.

However, the preparation of dinitrile compounds by hydrocyanation of an olefin such as butadiene can be carried out using a catalyst system in accordance with the invention for the above steps of formation of unsaturated nitrites and the above isomerization step, it being possible for the reaction consisting of hydrocyanation of unsaturated nitriles to dinitriles to be carried out with a catalyst system in accordance with the invention or any other catalyst system already known for this reaction.

Similarly the reaction consisting of hydrocyanation of the olefin to unsaturated nitrites and the isomerization thereof may be carried out with a catalyst system that is different from that of the invention, the step consisting of hydrocyanation of unsaturated nitriles to dinitriles being carried out with a catalyst system in accordance with the invention.

The following examples illustrate the invention.

In the examples, the abbreviations used have the meanings indicated below.

cod: 1,5-cyclooctadiene eq: equivalent

3PN: 3-pentenenitrile

4PN: 4-pentenenitrile

3+4PN: 3PN+4PN

DC(Y): degree of conversion of the product to be hydrocyanated, Y, corresponding to the ratio of the number of moles of Y converted to the initial number of moles of Y Linearity (L): ratio of the number of moles of adiponitrile (AdN) formed to the number of moles of dinitriles formed (sum of the moles of AdN, ethylsuccinonitrile (ESN) and methylglutaronitrile (MGN))

GC: gas chromatography ml: millilitre mol: mole(s)

mmol: millimole(s).

Ph: phenyl

EXAMPLE 1

Synthesis of Ligand A of Formula Below

For the preparation of ligand A, starting materials that are used are ortho-t-butylphenol and a phosphorochloridite for which the preparation process is described in an article by R. A. Sabirova, L. V. Nesterov, A. E. Arbuzov, published in *Zh. Obshch. Khim.* 1967, 37, 732-4, of formula below:

The procedure for preparing ligand A is as follows:

1.1 g of phosphorochloridite of formula above are dissolved in 5 ml of anhydrous tetrahydrofuran and 10 ml of anhydrous toluene, under argon, in a 100 ml round-bottomed flask. The solution is stirred at −10° C. The dropping funnel is charged with a solution of 600 mg of ortho-t-butylphenol and of 0.85 ml of triethylamine in 2 ml of anhydrous tetrahydrofuran, and this solution is introduced dropwise into the reaction medium maintained at −10° C.: a white precipitate forms. The suspension is vigorously stirred for 18 h at 25° C. and then filtered, under argon, on a bed of basic alumina I. After rinsing with toluene, the filtrate is concentrated under reduced pressure, to give 1.25 g of crude product in the form of a thick translucent oil. NMR analysis confirms the identity of the product obtained corresponding to the formula above.

EXAMPLE 2

Synthesis of a Ligand B of Formula Below

This ligand is prepared according to the same procedure as ligand A, using ortho-cresol. 1.67 g of the phosphorochloridite and 0.65 g of ortho-cresol giving, under these conditions, 1.27 g of product corresponding to the formula above.

EXAMPLE 3

Synthesis of a Ligand C of Formula Below

This ligand is prepared according to the same procedure as ligand A, using metal-cresol: 1.67 g of the phosphorochloridite and 0.65 g of meta-cresol giving, under these conditions, 1.57 g of the product corresponding to the formula above.

EXAMPLE 4

Synthesis of a Ligand D of Formula Below

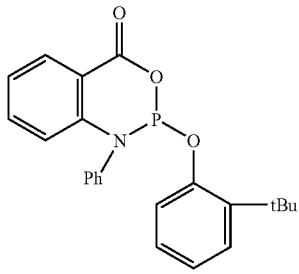

This ligand is obtained by reaction of ortho-t-butylphenyl with a phosphorochloridite of formula below:

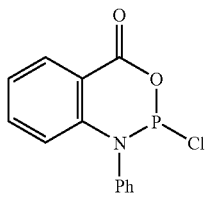

This phosphorochloridite is prepared according to the following procedure:

15 ml of $PCl_3$ are added to 10.7 g of N-phenyl-anthranilic acid, followed by 20 ml of anhydrous toluene, under argon, in a 100 ml round-bottomed flask. The thick suspension thus obtained is stirred for 1 h at 25° C. and then gradually brought to 60° C. and, finally, refluxed for 3 h. The solution thus obtained is cooled to ambient temperature, filtered under an inert atmosphere and concentrated under reduced pressure. A red solid is obtained, which is purified by trituration in pentane and then filtration under an inert atmosphere. 12.5 g of a red solid approximately 85% pure are recovered.

The procedure for preparing ligand D is as follows:

1.1 g of the phosphorochloridite of formula above are dissolved in 5 ml of anhydrous tetrahydrofuran and 10 ml of anhydrous toluene, under argon, in a 100 ml round-bottomed flask. The solution is stirred at −10° C. The dropping funnel is charged with a solution of 600 mg of ortho-t-butylphenol and of 0.85 ml of triethylamine in 2 ml of anhydrous tetrahydrofuran, and this solution is introduced dropwise into the reaction medium maintained at 10° C.: the initially red solution loses its colour, and a yellow precipitate forms. The suspension is stirred vigorously for 18 h at 25° C. and filtered, under argon, on a bed of basic alumina I. After rinsing with toluene, the filtrate is concentrated under reduced pressure, to give 1.3 g of crude product in the form of a thick translucent oil. NMR analysis confirms the identity of the product obtained corresponding to the formula above.

EXAMPLE 5

Synthesis of a Ligand E of Formula Below

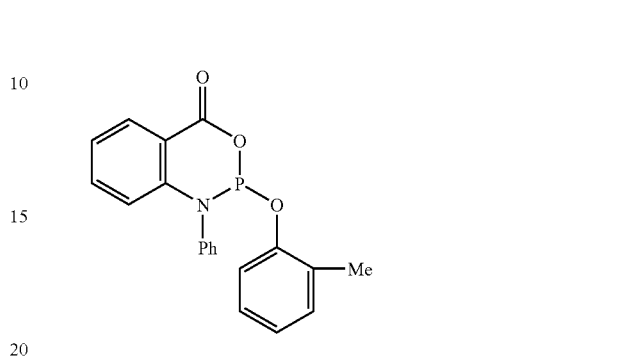

This ligand is prepared according to the same procedure as ligand D, using ortho-cresol: 1.67 g of the phosphorochloridite and 0.65 g of ortho-cresol giving, under these conditions, 1.56 g of the product corresponding to the formula above.

EXAMPLE 6

Synthesis of a Ligand F of Formula Below

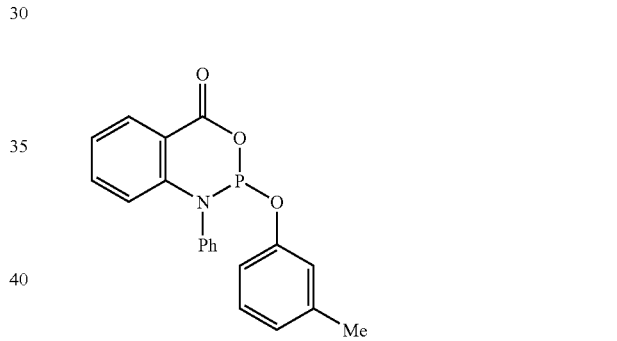

This ligand is prepared according to the same procedure as ligand D, using meta-cresol: 1.67 g of the phosphorochloridite and 0.65 g of meta-cresol give, under these conditions, 1.57 g of the product corresponding to the formula above.

EXAMPLE 7

Hydrocyanation of 3-pentenenitrile (3PN) to adiponitrile (AdN)

A 60 ml Shott-type glass tube equipped with a septum stopper is successively charged, under an argon atmosphere, with:

the ligand (2.5 eq),
1.21 g (15 mmol; 30 eq) of anhydrous 3PN,
138 mg (0.5 mmol; 1 eq) of Ni(cod)$_2$, and
68 mg (0.5 mmol; 1 eq) of zinc(II) chloride.

The mixture is brought to 70° C. with stirring. Acetone cyanohydrin is injected into the reaction medium by means of a syringe pump at a flow rate of 0.45 ml per hour. After injection for 3 hours, the syringe pump is stopped. The mixture is cooled to ambient temperature, diluted with acetone, and analysed by gas chromatography.

Under these conditions, the following results are obtained:

| Ligand | DC(3PN) | Linearity |
|---|---|---|
| A | 36% | 44% |
| B | 12% | 34% |
| C | 24% | 74% |
| D | 32% | 53% |
| E | 10% | 72% |
| F | 8% | 69% |

The invention claimed is:

1. A process, for hydrocyanating an ethylenically unsaturated nitrile compound to dinitrile, comprising the step of reacting said nitrile with hydrogen cyanide, in the presence of a catalyst system comprising:
at least one transition metal compound,
at least one compound of formula (I) below:

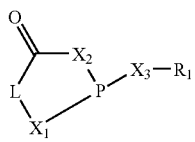

wherein:
$X_1$ and $X_2$, which are identical or different, represent an oxygen atom or the divalent radical NR2, wherein R2 represents a hydrogen atom, an alkyl, aryl, sulphonyl, cycloalkyl or carbonyl radical, ,
$X_3$ represents a covalent bond, an oxygen atom or the divalent radical NR2, wherein R2 represents a hydrogen atom, an alkyl, aryl, sulphonyl, cycloalkyl or carbonyl radical,
the radical $R_1$ represents a linear or branched alkyl radical having from 1 to 12 carbon atoms optionally having hetero atoms, or a substituted or unsubstituted aromatic or cycloaliphatic radical optionally having hetero atoms or one or more rings in fused or nonfused form, and
L represents a substituted or unsubstituted aromatic having one ring in fused form, and
a cocatalyst consisting of at least one Lewis acid.

2. The process according to claim 1, wherein the ethylenically unsaturated nitrile is a linear pentenenitrile.

3. The process according to claim 2, wherein the linear pentenenitrile contain amounts of other compounds selected from the group consisting of 2-methyl-3-butenenitrile, 2-methyl-2-butenenitrile, 2-pentenenitrile, valeronitrile, adiponitrile, 2-methylglutaronitrile, 2-ethylsuccinonitrile and butadiene.

4. process according to claim 1, wherein the Lewis acid used as cocatalyst has an element of groups Ib, IIb, IIIa, IIIb, IVa, IVb, Va, Vb, VIb, VIIB or VIII of the Periodic Table of Elements.

5. The process according to claim 1, wherein the Lewis acid is a salt selected from the group consisting of halides, sulphates, sulphonates, haloalkylsulphonates, perhaloalkylsulphonates, haloalkylacetates, perhaloalkylacetates, carboxylates and phosphates bromide.

6. The process according to claim 5, wherein the Lewis acid is zinc chloride, zinc bromide, zinc iodide, manganese chloride, manganese bromide, cadmium chloride, cadmium bromide, stannous chloride, stannous bromide, stannous sulphate, stannous tartrate, indium trifluoromethylsulphonate, indium trifluoromethyl acetate, lanthanum chloride, cerium chloride, praseodymium chloride, neodymium chloride, samarium chloride, europium chloride, gadolinium chloride, terbium chloride, dysprosium chloride, hafnium chloride, erbium chloride, thallium chloride, ytterbium chloride, lutetium chloride, lanthanum bromide, cerium bromide, praseodymium bromide, neodymium bromide, samarium bromide, europium bromide, gadolinium bromide, terbium bromide, dysprosium bromide, hafnium bromide, erbium bromide, thallium bromide, ytterbium bromide, lutetium bromide, cobalt chloride, ferrous chloride or yttrium chloride.

7. The process according to claim 1, wherein the Lewis acid represents from 0.01 to 50 mol per mole of transition metal compound.

8. The process according to claim 1, wherein further comprising the step of carrying out an isomerization reaction of 2-methyl-3-butenenitrile, present in a reaction mixture originating from the hydrocyanation of butadiene to pentenenitriles, in the absence of hydrogen cyanide, by working in the presence of a catalyst comprising at least one compound of formula (I) and at least one transition metal compound.

9. The process according to claim 8, wherein the 2-methyl-3-butenenitrile subjected to the isomerization is used alone or as a mixture with 2-methyl-2-butenenitrile, 4-pentenenitrile, 3-pentenenitrile, 2-pentenenitrile, butadiene, adiponitrile, 2-methylglutaronitrile, 2-ethylsuccinonitrile or valeronitrile.

10. The process according to claim 8, wherein the isomerization reaction is carried out at a temperature of 10° C. to 200° C.

11. The process according to claim 8, wherein the isomerization of the 2-methyl-3-butenenitrile to pentenenitriles is carried out in the presence of at least one transition metal compound and of at least one organophosphorus compound of formula (I).

12. The process according to claim 1, wherein $X_1$ and $X_2$ are different and represent equally an oxygen atom or a divalent radical NR2; and $X_3$ represents an oxygen atom.

13. The process according to claim 1, wherein the compounds of general formula (I) are selected from the group consisting of the compounds of formulae below:

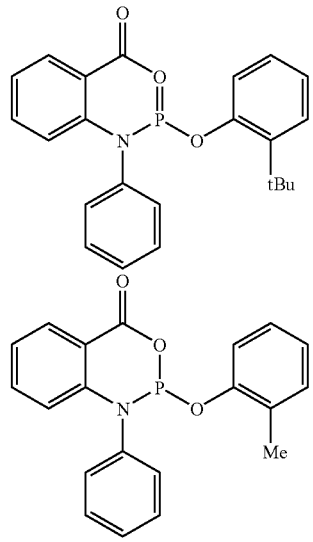

-continued

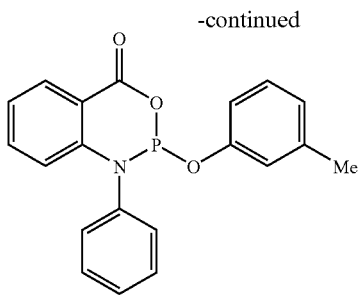

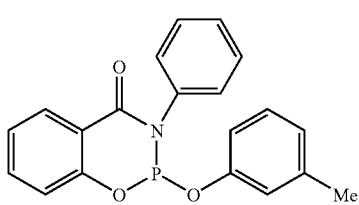

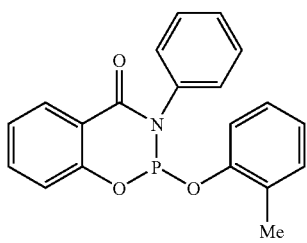

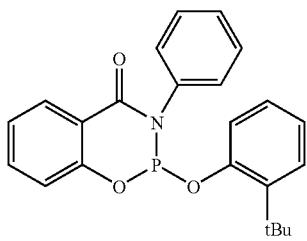

-continued

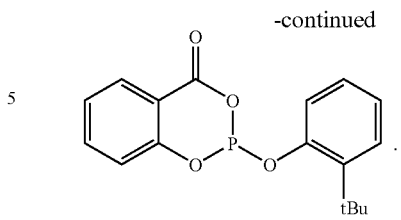

14. The process according to claim 1, wherein the catalyst system corresponds to general formula (V):

$$M[L_f]_t \qquad (V)$$

wherein:

M is a transition metal, $L_f$ represents the organophosphorus ligand of formula (I), and t represents a number between 1 and 6 (limits inclusive).

15. The process according to claim 14, wherein the catalyst system is a nickel compound in which nickel is in oxidation state zero, or a compound of nickel.

16. The process according to claim 14, wherein the catalyst system is potassium tetracyanonickelate $K_4$ $_{[Ni(CN)4]}$, bis (acrylonitrile)nickel zero, bis(cycloocta-1,5-diene)nickel, tetrakis(triphenylphosphine)nickel zero.

17. The process according to claim 14, wherein the catalyst system is a nickel compound selected from the group consisting of nickel carboxylate, nickel carbonate, nickel bicarbonate, nickel borate, nickel bromide, nickel chloride, nickel citrate, nickel thiocyanate, nickel cyanide, nickel formate, nickel hydroxide, nickel hydrophosphite, nickel phosphite, nickel phosphate, nickel iodide, nickel nitrate, nickel sulphate, nickel sulphite, nickel arylsulphonate, and nickel alkylsulphonate.

18. The process according to claim 1, wherein the catalyst system is used in an amount such that there is, per mole of organic compound to be hydrocyanated or isomerized, between $10^{-4}$ and 1 mol of the transition metal, and in that the compound of formula (I) is such that the number of moles of this compound, relative to 1 mol of transition metal, is from 0.5 to 500.

19. the process according to claim 1, wherein the hyrocyantion reaction temperature is between 10° C. and 200° C.

* * * * *